(12) United States Patent
Watson et al.

(10) Patent No.: US 6,346,198 B1
(45) Date of Patent: Feb. 12, 2002

(54) SYSTEM FOR FLUID STREAM TREATMENT USING FEED FORWARD OF ANALYSIS OF A DIVERTED TREATED PILOT STREAM

(75) Inventors: Les Watson, Auburn; Stephen J. Armstrong, Meadow Vista, both of CA (US)

(73) Assignee: Industrial Control Systems, Auburn, CA (US)

( * ) Notice: Subject to any disclaimer, the term of this patent is extended or adjusted under 35 U.S.C. 154(b) by 0 days.

(21) Appl. No.: 09/557,989

(22) Filed: Apr. 25, 2000

(51) Int. Cl.[7] .............................. B01D 17/12; C02F 1/50
(52) U.S. Cl. .................... 210/739; 210/87; 210/96.1; 210/198.1; 210/754; 436/52; 436/55
(58) Field of Search .............................. 210/85, 87, 96, 210/1, 101, 103, 139, 143, 198.1, 739, 746, 754, 764, 752; 422/62; 436/39, 52, 55, 174, 180; 137/3, 93; 366/151.1, 152.17

(56) References Cited

U.S. PATENT DOCUMENTS

| | | | |
|---|---|---|---|
| 4,435,291 A | 3/1984 | Matsko | ........................ 210/734 |
| 5,011,613 A | 4/1991 | Feray | |
| 5,057,229 A | 10/1991 | Schulenburg | |
| 5,108,929 A | 4/1992 | Segura | |
| 5,196,111 A | 3/1993 | Nicol | |
| 5,256,307 A | 10/1993 | Bachhofer | |
| 5,422,014 A | 6/1995 | Allen | |
| 5,540,845 A | 7/1996 | Blanchard | |
| 5,869,342 A | * 2/1999 | Stannard et al. | ............... 436/55 |
| 6,129,104 A | * 10/2000 | Ellard et al. | .................... 137/3 |

\* cited by examiner

Primary Examiner—Joseph W. Drodge
(74) Attorney, Agent, or Firm—Heisler & Associates

(57) ABSTRACT

A system is provided for controlling a rate at which a treatment fluid is introduced into a main stream to be treated so that a selected characteristic of the main stream matches a set point for the selected characteristic. A pilot stream is diverted from the main stream. The pilot stream is treated with a known amount of the treatment fluid and is analyzed to determine if the selected characteristic matches the set point for the selected characteristic. If the set point for the selected characteristic is matched in the pilot stream, a related amount of treatment fluid is introduced into the main stream. If analysis of the pilot stream indicates that the level of the selected characteristic is above or below the set point, the rate at which the treatment fluid is injected into the pilot stream and the main stream is appropriately adjusted to cause the selected characteristic in the pilot stream and the main stream to more closely match the set point for the selected characteristic. The selected characteristic can optionally be the treatment fluid which remains after the treatment fluid has been utilized to neutralize an undesirable characteristic of the fluid within the main stream.

20 Claims, 2 Drawing Sheets

SYSTEM FOR FLUID STREAM TREATMENT USING FEED FORWARD OF ANALYSIS OF A DIVERTED TREATED PILOT STREAM

FIELD OF THE INVENTION

The following invention relates to fluid control systems which are configured to control the introduction of a treatment fluid into a fluid stream to cause a selected characteristic of the fluid stream to match a desired level. More particularly, this invention relates to treatment fluid injection control systems which divert a pilot stream from the fluid stream, treat the pilot stream with the treatment fluid, analyze the pilot stream downstream from the point of introduction of the treatment fluid and use the results of this analysis to control a main treatment fluid inlet into the fluid stream.

BACKGROUND OF THE INVENTION

Many fluid handling systems require monitoring of selected characteristics of the fluid stream to control the introduction of treatment fluids into the fluid stream. For instance, in waste water treatment facilities a main stream of waste water typically is treated with a chlorine containing compound, such as sodium hypochlorite, to neutralize bacteria in the waste water stream. It is undesirable to undertreat the waste water stream because active bacteria will thus remain in the waste water stream. It is also undesirable to overtreat the waste water with chlorine because a residual chlorine level in the waste water stream will be detrimentally high. Additionally, the chlorine or other treatment fluid is wasted and additional chemical is typically needed to neutralize the excess chlorine.

Many advanced waste water treatment systems include a residual chlorine analyzer downstream from the chlorinator which monitors the levels of chlorine residual remaining in the waste water stream. Controllers are known which utilize the results of this downstream analyzer to provide a feedback signal to the chlorinator. In essence, if an amount of residual chlorine is too high at the downstream analyzer, the chlorinator receives a feedback signal which decreases the rate of introduction of chlorine. If the analyzer detects that no chlorine or too little chlorine remains, indicative that not all of the bacteria has been neutralized, the feedback signal will cause the chlorinator to increase the rate with which it introduces chlorine.

While such residual chlorine analyzers and feedback control systems are generally effective, they suffer from numerous drawbacks. For instance, when the analyzer detects a less than optimal amount of chlorine residual, additional treatment must still occur to the waste water stream to properly treat the waste water. The delay associated with the distance between the analyzer and the chlorinator and the amount of time it takes for the chlorine analyzer to detect any change in chlorine residual causes problems in the control. Such feedback systems have a tendency to enter into an oscillatory state between over and under chlorination which only relatively slowly resolves itself, especially when the chemical requirement within the waste water stream is fluctuating. Waste water treatment facilities can incur fines for releasing waste water which is either undertreated or overtreated with chlorine containing compounds. Waste water treatment facilities additionally suffer financially from the unnecessary use of excess chlorine and chlorine neutralizing chemicals, such as sulphur dioxide when the chlorination system is not operating optimally.

Other fluid control systems exhibit a need corresponding to that identified above. Specifically, systems which require treatment of a main stream with a treatment fluid to cause a selected characteristic of the main fluid stream to match a desired level/set point, often cannot be effectively controlled by having an analyzer downstream from the treatment fluid injection site which feeds back a signal to the treatment fluid injection site. Accordingly, a need exists for a system for fluid stream treatment which can accurately predict the amount of treatment fluid required for a main fluid stream in advance and feed this information forward to the treatment fluid injection site to minimize the amount of treatment fluid necessary to effectively treat the fluid stream in a precise fashion.

SUMMARY OF THE INVENTION

The system of this invention precisely controls the amount of treatment fluid to be introduced into a main fluid stream to cause a selected characteristic of the main fluid stream to match a desired set point for the selected characteristic in the main fluid stream. A pilot stream is diverted out of the main fluid stream at a location upstream from the main treatment fluid injection site in the main fluid stream. This pilot stream has a pilot treatment fluid injector which injects a known amount of the treatment fluid into the pilot stream. The treatment fluid acts on the pilot stream and then an analyzer samples the pilot stream downstream from the pilot treatment fluid injector.

The analyzer measures the level of the selected characteristic present in the pilot fluid stream. The result of this analysis is communicated to a controller which controls both the pilot treatment fluid injector and the main treatment fluid injector within the main fluid stream. If the pilot stream analyzer detects that a level of the selected characteristic is below a set point for the selected characteristic, the pilot treatment fluid injector is adjusted to increase the amount of treatment fluid injected into the pilot stream. If the analyzer detects an excess amount of the selected characteristic above the set point, the controller causes an amount of the treatment fluid injected into the pilot stream to be decreased.

When the analyzer detects a level of the selected characteristic matching the set point for the selected characteristic, or within the range desired by the operator, the controller maintains the rate of injection of the treatment fluid into the pilot stream. The controller additionally adjusts a rate of treatment fluid injection at the main fluid stream treatment fluid injector to correspond to the pilot treatment fluid injector rate. Specifically, the arithmatic product of the rate of injection of the treatment fluid from the pilot treatment fluid injector into the pilot stream and the ratio of the flow rate of the pilot stream to the ratio of the main fluid stream is used to set the flow rate for the treatment fluid into the main fluid stream.

If the characteristics of the main fluid stream are changing, the pilot stream will reflect these changes and the pilot treatment fluid injector, pilot stream analyzer and controller will appropriately adjust to properly neutralize the pilot stream. Once adjusted, a level for the main treatment fluid injector in the main treatment fluid stream is used to adjust the main treatment fluid injector so that the main fluid stream is properly neutralized in a way that reflects changes in the characteristics of the fluid within the main fluid stream.

A verification analyzer can optionally be provided downstream from the main treatment fluid injector to verify that the selected characteristic within the main fluid stream is at the set point. Data associated with settings for the fluid treatment injectors and the pilot stream and the main stream and levels of selected characteristics within the pilot stream and the main stream, as well as flow rates for the pilot stream and the main stream can all be outputted relative to time for analysis by the operator to verify that the system is operating properly.

When the main fluid stream is a waste water stream and bacteria within the waste water stream is to be neutralized, the treatment fluid is typically a chlorine containing compound, such as sodium hypochlorite, and the selected characteristic is the level of residual chlorine existing within the waste water after treatment with the chlorine containing compound.

OBJECTS OF THE INVENTION

Accordingly, a primary object of the present invention is to provide a system for adjusting a rate of introduction of treatment fluid into a main fluid stream which precisely causes a selected characteristic of the main fluid stream to match a set point for the selected characteristic.

Another object of the present invention is to provide a fluid treatment system which minimizes an amount of treatment fluid required.

Another object of the present invention is to provide a system for treating waste water which reliably treats the waste water with chlorine without over chlorinating or under chlorinating the waste water.

Another object of the present invention is to provide a fluid control system which can operate with a minimum of operator monitoring and intervention.

Another object of the present invention is to provide a fluid treatment system which can display and record data associated with analysis of selected characteristics of the fluid stream for review by an operator.

Another object of the present invention is to provide a waste water treatment system which utilizes residual chlorine analyzers to control a rate of introduction of chlorine into a waste water stream.

Other further objects of the present invention will become apparent from a careful reading of the included drawing figures, the claims and detailed description of the invention.

DESCRIPTION OF THE PREFERRED EMBODIMENT

Figure 1:
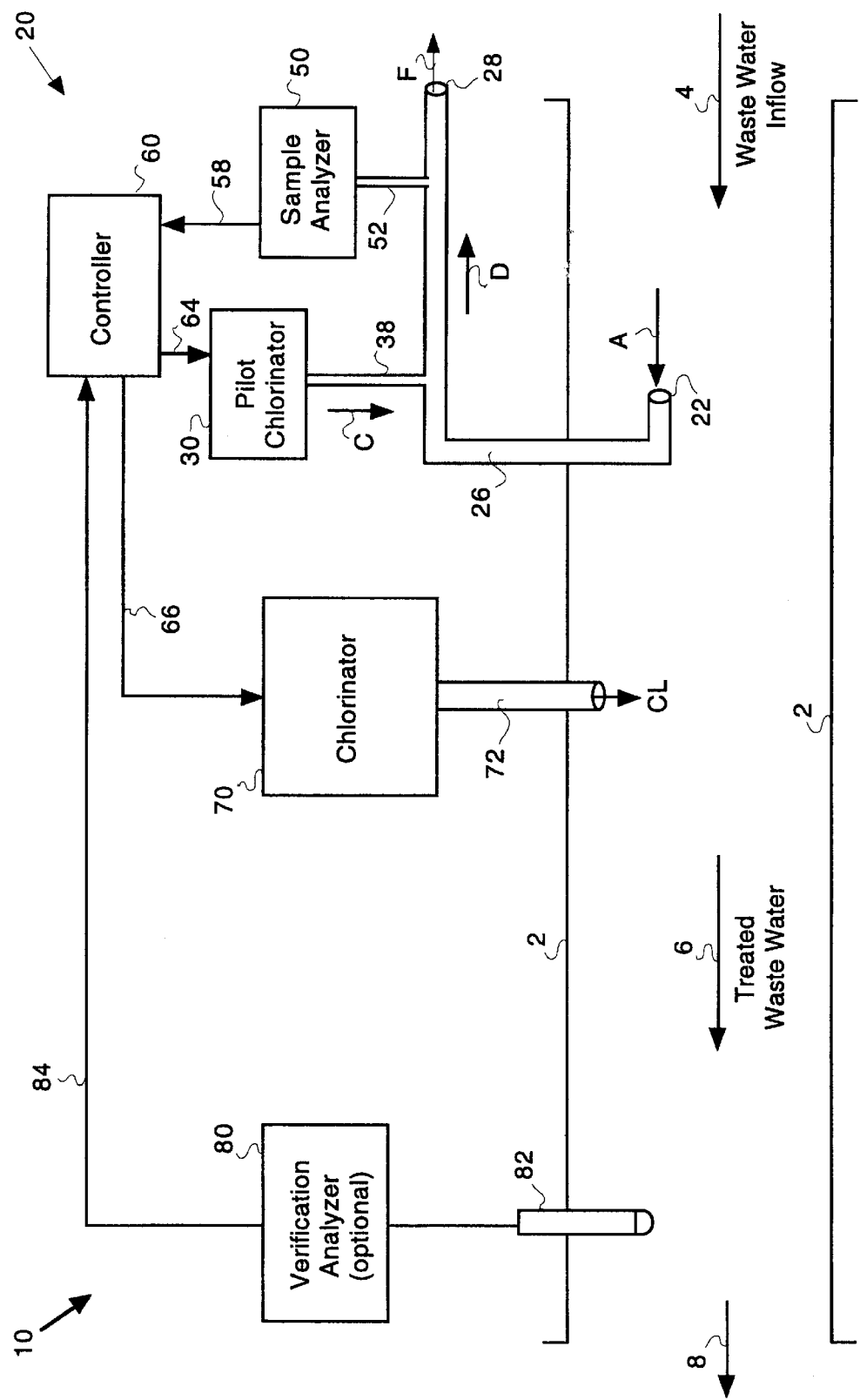
FIG. 1 is a schematic diagram illustrating the major components of the system of this invention as they would exist when incorporating the system of this invention into a waste water treatment system.

Referring to the drawings, wherein like reference numerals represent like parts throughout the various drawing figures, reference numeral 10 is directed to a system for treatment of a fluid stream, such as waste water passing through a conduit 2, using feed forward of analysis of characteristics of a pilot subsystem 20 diverted from the conduit 2. The system 10 is described in its preferred embodiment in the context of a waste water treatment system but is equally applicable to other fluid stream treatment systems where a treatment fluid is added to a main fluid stream if desired to exhibit a specified amount of a selected characteristic. Hence, this detailed description should not be construed as limiting this invention merely to waste water treatment systems.

In essence, and with particular reference to FIG. 1, the basic details of the system 10 are described. A main conduit 2 having waste water 4 passing therethrough is treated in a controlled fashion according to the system 10 of this invention. A pilot subsystem 20 diverts a portion of the waste water inflow 4 away from the conduit 2 and along a treatment pathway 26. A pilot chlorinator 30 injects a precisely measured amount of a chlorine containing compound into the treatment pathway 26 of the pilot subsystem 20. After the chlorine has time to react with the waste water within the treatment pathway 26, a sample analyzer 50 samples the waste water passing through the treatment pathway 26 to evaluate the amount of chlorine residual remaining in the treatment pathway 26.

The result of the analyzer 50 analysis is fed to a controller 60. The controller 60 adjusts a rate of injection of chlorine delivered by the pilot chlorinator 30 into the treatment pathway 26 of the pilot subsystem 20. If the analyzer 50 detects too much residual chlorine, the rate of chlorine injection from the pilot chlorinator 30 is decreased. If the analyzer 50 detects too little residual chlorine, the controller 60 causes the pilot chlorinator 30 to increase an amount of chlorine injected into the treatment pathway 26. If the analyzer 50 detects an amount of residual chlorine which matches a desired set point for residual chlorine, the controller 60 maintains a rate of injection provided by the pilot chlorinator 30.

Additionally, the controller 60 sends a control signal to a main chlorinator 70 configured to inject a chlorine containing compound into the main stream conduit 2 of the system 10. In essence, the controller 60 causes the chlorinator 70 to inject an amount of chlorine into the main stream conduit 2 which is equal to the arithmatic product of the rate of chlorine delivered by the pilot chlorinator 30 and the ratio of flow rates of waste water passing through the treatment pathway 26 of the pilot subsystem 20 and waste water passing through the main stream conduit 2. Thus, the chlorinator 70 provides precisely the appropriate amount of chlorine required to neutralize the waste water stream passing through the main stream conduit 2. A verification analyzer 80 can optionally be provided downstream from the chlorinator 70 which verifies that the level of chlorine residual in the treated waste water 6 passing through the main stream conduit 2 matches the set point defining the desired level of residual chlorine, before the waste water exits the conduit 2 through the outflow 8.

Figure 2:
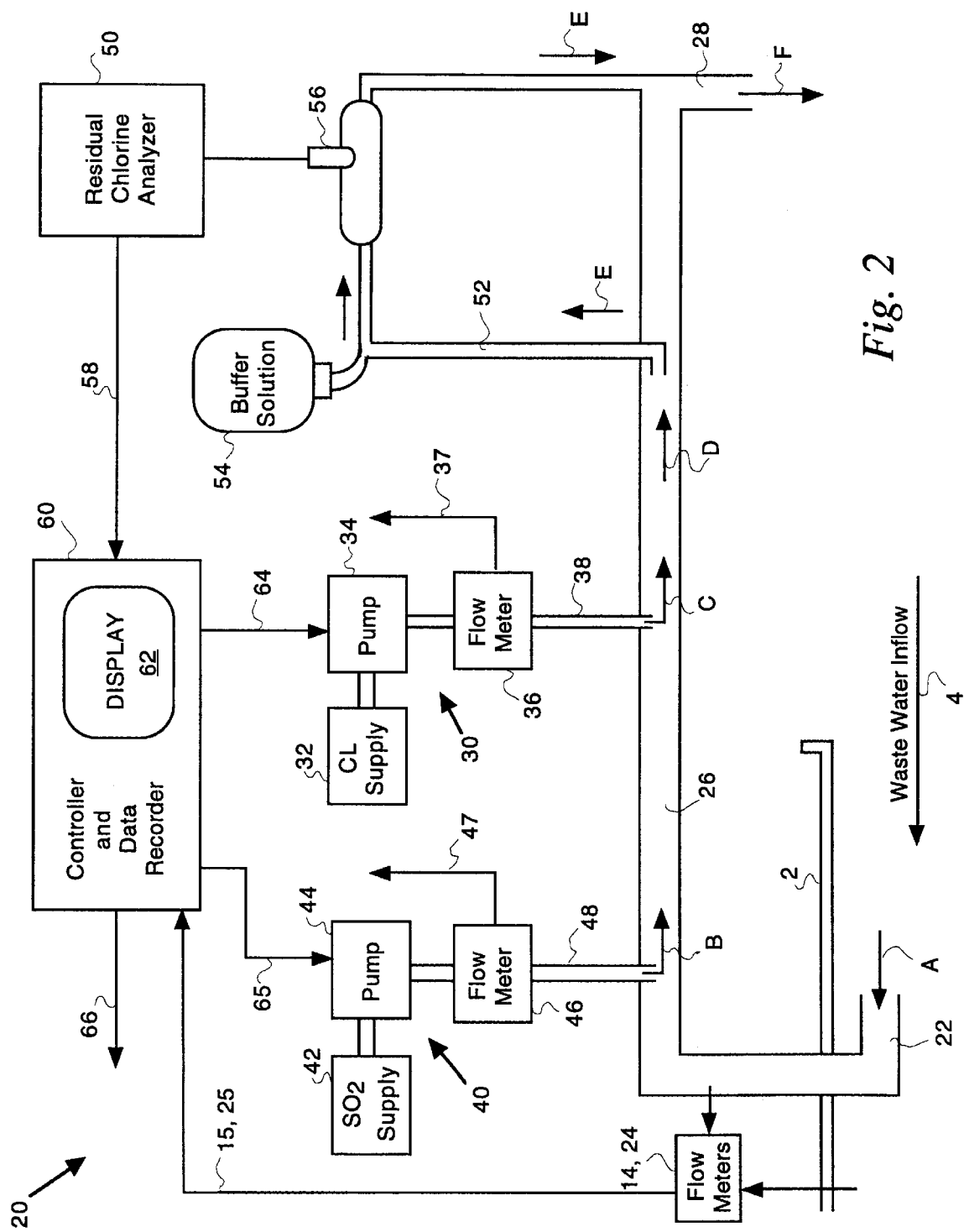
FIG. 2 is a schematic diagram illustrating the details of a pilot stream portion of that which is shown in FIG. 1.

More specifically, and with particular reference to FIG. 2, details of the pilot subsystem 20 of the system 10 of this invention are described. The pilot subsystem 20 includes an inlet port 22 within the main stream conduit 2, capable of diverting a portion of the waste water inflow 4, along arrow A, into the pilot subsystem 20. The waste water passing through the pilot subsystem 20 travels along the treatment pathway 26.

A flow sensor 24 is located along the treatment pathway 26 to accurately measure the rate of flow of waste water passing through the pilot subsystem 20. The flow sensor 24 generates a pilot flow rate signal 25 which is returned to the controller 60 to assist in operating the system 10 of this invention. A flow meter 14 is also located on the main stream conduit 2 which generates a process flow rate signal 15 which is also sent to the controller 60 as part of the system 10 of this invention. While the flow meters 14, 24 can be separate and return separate signals 15, 25 to the controller 60. It is also possible that flow meters 14, 24 can be integrated together so that they actually measure a ratio of pilot subsystem 20 flow rate to main stream 2 flow rate and send a single signal 15, 25 representative of this ratio of flow rates. This ratio establishes the "gain" in the system 10 necessary to cause the chlorinator 70 to operate at an appropriately greater rate than the rate of the pilot chlorinator 30 when the system 10 of this invention is analogized to an amplifier.

The pilot chlorinator 30 is configured to inject a chlorine containing compound, preferably sodium hypochlorite, into the waste water passing through the treatment pathway 26 of the pilot subsystem 20. The pilot chlorinator 30 includes a chlorine supply 32 coupled to a pump 34 in line with a flow meter 36 and leading to a chlorine injection line 38 which extends into the treatment pathway 26. The flow meter 36 generates a feedback signal 37 which is returned to the controller 60. This feedback signal 37 essentially is representative of the rate at which the chlorine containing compound is injected into the treatment pathway 26 along arrow C. The pump 34 has a flow rate thereof controlled by the controller 60. Preferably, the pump 34 is of a type which can be precisely throttled so that the rate of delivery of chlorine by the pilot chlorinator 30 into the treatment pathway 26 of the pilot subsystem 20 can be precisely controlled.

The point where the chlorine injection line 38 of the pilot chlorinator 30 enters into the treatment pathway 26 defines a first location in the pilot stream where the treatment fluid, preferably sodium hypochlorite, enters into the pilot stream. Organic and inorganic components within the waste water then react with the chlorine. Some residence time is provided between the chlorine injection in the waste water, arrow D, to allow the organic and inorganic components to be neutralized. If necessary, this portion of the treatment pathway 26 can be appropriately elongated or configured with a mixing device or a reaction catalyst to accelerate the rate of neutralization.

If all of the chlorine is used up in neutralizing the undesirable components of the waste water, it is difficult to determine whether precisely the right amount of chlorine was utilized to neutralize the waste water. Hence, it is desirable to slightly overtreat the waste water and leave a small amount of residual chlorine in the waste water. This small residual amount of chlorine present after sufficient reaction time to neutralize the waste water, indicates that all of the waste water bacteria or other undesirable components have been neutralized. Additionally, when a small amount of residual chlorine remains in the waste water passing through the treatment pathway 26, this residual chlorine can define a selected characteristic which can then be monitored at a second downstream location by the analyzer 50.

The analyzer 50 determines whether a proper amount of chlorine has been introduced into the pilot stream so that the selected characteristic to be monitored, preferably residual chlorine, is at or sufficiently near a set point defining the desired amount of residual chlorine remaining in the waste water stream. Hence, the amount of neutralization in the waste water does not need to be directly measured, but rather the remaining presence of the neutralizing agent, preferably the sodium hypochlorite, can be monitored. In other fluid control systems where it is desirable to monitor residual amounts of some other treatment fluid, rather than directly monitoring the main stream for other characteristics, the system of this invention is particularly adaptable.

After sufficient residence time between the chlorine and the waste water has occurred (along arrow D) the sample analyzer 50 is then utilized to measure the chlorine residual remaining in the waste water. Specifically, a sample bypass line 52 preferably diverts a portion of the waste water to be analyzed, along arrow E. Utilizing known residual chlorine analysis techniques, the waste water is then monitored to measure the amount of chlorine residual remaining in the waste water. Typically, this analyzer 50 would require a buffer solution 54 to be added to the sample bypass line 52 and then a sample cell 56 would measure the appropriately buffered waste water sample.

The analyzer 50 generates a feedback signal 58 indicating the amount of chlorine remaining in the pilot subsystem 20 downstream from the pilot chlorinator 30. The sample bypass line 52 then rejoins the treatment pathway 26 where it terminates in an outlet port 28.

The waste water exiting out of the outlet port 28, along arrow F, can be returned to the environment when the system 10 is operating within desired parameters and the analyzer 50 is indicating that an acceptable level of chlorine residual remains in the waste water. When the system 10 is adjusted to match the amount of treatment fluid necessary to neutralize the waste water, the waste water exiting out of the outlet port 28 is preferably returned into the main stream conduit 2 or otherwise additionally treated before exiting the system 10.

Preferably, the pilot subsystem 20 additionally includes a sulphur dioxide (SO2) injection subsystem 40. While not strictly required, it is desirable to have the SO2 injection subsystem for various reasons. First, the SO2 injection subsystem allows SO2 to be introduced into the pilot subsystem 20 to assist in calibrating the pilot chlorinator 30 and the analyzer 50. Specifically, SO2 and chlorine neutralize each other and so SO2 can represent inorganic bacteria chlorine demand in waste water to calibrate and startup the pilot subsystem 20.

Additionally before waste water may be discharged into lakes, streams or estuaries it must be verified that no chlorine residual remains in the waste stream. This is typically done by monitoring the chlorine residual just as it leaves the waste water treatment plant by means of a chlorine residual analyzer. The analyzer sends a signal to a sulphur dioxide (SO2) controller. The SO2 controller then supplies a signal to the main sulphanator.

If the SO2 controller senses any chlorine residual above its set point it increases the amount of SO2 into the waste stream to neutralize the chlorine. One disadvantage to this approach is that chlorine residual analyzers are unstable when measuring low levels of chlorine. This sometimes results in ineffective control in the form of over and under dechlorination it may result in fines by the regulating authorities. Using the system of this invention, the SO2 injection subsystem 40 may be used analogously to the pilot chlorination subsystem 30.

This is accomplished by sampling the waste stream down stream of main chlorination injection point and very near the effluent path of the treatment plant. When used in this manner, the pilot chlorinator 30 and the pilot sulphanator 40 are reversed in position hydraulically (FIG. 2).

In the pilot treatment path 26, the pilot chlorine injection point arrow C is now upstream of the pilot SO2 injection point arrow B.

Reference FIG. 2, the chlorinated waste stream enters inlet port 22 and travels through pilot treatment pathway 26 where the pilot subsystem 20 causes injection of SO2 to neutralize any excess chlorine residual.

The chlorine residual analyzer 50 in pilot subsystem 20 sends the value of the chlorine residual in pilot pathway 26 to the controller 60 through feedback path 58.

The controller 60 sends an output signal 65 to the pilot sulphanator subsystem 40. The pilot sulphanator then increases or decreases as necessary the amount of SO2 injected so as to maintain the set point in controller 60.

The controller 60 also sends an output signal 66 to a main sulphanator analogous to the main chlorinator 70 which in turn injects into the main chlorinated waste stream 4 the precise amount of SO2 needed to neutralize chlorine in the waste system.

Typically a small level of SO2 residual is factored in to assure no chlorine residual level is possible.

The flow ratios of pilot stream to main stream flows and pilot stream treatment fluid to main stream treatment fluid are maintained in the dechlorination system of the invention as were discussed in the chlorination system of the invention.

Also, in a manner similar to that discussed in the chlorination system of the invention where the SO2 injection subsystem was used as a calibration aid, the chlorine injection subsystem may be used as a calibration aid for the dechlorination system of the invention.

One note of difference in these two systems is that the controller 60 for the chlorine injection subsystem 30 is configured to be reverse acting. That is an increase in chlorine residual detected by the chlorine residual analyzer 50 will cause a decrease in chlorine injection. Whereas the Controller 60 for the SO2 injection subsystem is direct acting. That is an increase in chlorine residual detected by the chlorine residual analyzer 50 will cause an increase in the injection of SO2.

The controller 60 preferably is in the form of at least one application specific integrated circuit which is configured using known techniques to receive the various different inputs identified above and to make adjustments to the system 10 to achieve results desired by an operator. The controller 60 preferably additionally includes a display 62 and also an output system for printing onto paper or other media a hard copy for recording data indicative of the overall performance of the various different portions of the system 10.

The controller 60 receives as input the residual free chlorine detected by the analyzer 50 along feedback signal 58. The controller 60 may also receive the rate of chlorine injection by the pilot chlorinator 30 along feedback signal 37, the rate of SO2 injection from the SO2 injection subsystem 40 along feedback signal 47, and the ratio of flow rates between the pilot subsystem 20 and the main stream conduit 20 along flow rate signal 15, 25.

The controller 60 additionally includes a set point, typically provided by the operator, indicating the desired level of residual chlorine. This set point can either be a single point or can be configured as an acceptable range or a tolerance level above and below the single set point. Further, the controller 60 can be programmed by the operator to control what information is represented on the display 62 and what information is recorded and outputted by data recorder/printer outputs provided by the controller 60. Other settings and initial settings for the pilot chlorinator 30, SO2 injection subsystem 40 and chlorinator 70 can be provided by the operator. Finally, the controller 60 receives an optional verification signal 84 from the verification analyzer 80 which utilizes a probe 82 to measure an amount of chlorine residual adjacent the outflow 8 of the main stream conduit 2. This optional verification signal 84 can be utilized merely to verify that the pilot subsystem 20 is operating as desired so that the controller 60 is setting the injection rate of the main chlorinator 70 appropriately.

The controller 60 has appropriate logic provided by the application specific integrated circuit, or other logic devices, such as software operating within a personal computer or other programmable computing device, which act on the inputs provided by the operator and the signals received from the various different portions of the pilot subsystem 20 to generate various different output signals. First, the controller 60 provides an outlet pilot chlorinator signal 64 which is coupled to the chlorine pump 34 to cause the chlorine pump 34 to adjust a rate at which the pilot chlorinator 30 injects chlorine into the pilot subsystem 20. Second, the controller 60 produces an SO2 output pilot control signal 65 which adjusts a rate at which the SO2 pump 44 delivers SO2 into the pilot subsystem 20. Finally, the controller 60 generates a feed forward process control signal 66 which is directed to the chlorinator 70 and throttles a rate at which the chlorinator 70 delivers chlorine out of the main chlorine injector 72 and into the main stream conduit 2. Also, the controller 60 can generate a feedforward process signal which is directed to main sulphanator described above and throttles a rate at which the sulphanator delivers SO2 out of the main SO2 injector and into the main stream conduit 2.

Preferably, the logic within the controller 60 generates the feedback pilot control signal 64 in a manner which corresponds to the feed forward process control signal 66 except that these signals 64, 66 vary based on the ratio of flow rate in the pilot subsystem 20 and the main stream conduit 2, as indicated by the flow meters 14, 24. Hence, when the analyzer 50 is indicating that the desired level of residual chlorine exists in pilot subsystem 20, the feed forward process control signal 66 corresponds to the feedback pilot control signal 64 which is merely keeping the rate of chlorine injection into the pilot subsystem 20 constant, multiplied by the ratio of flow rates between the pilot subsystem 20 and the main stream conduit 2.

Optionally, when the analyzer 50 is detecting a level of residual free chlorine which is either too high or too low, the controller 60 increases or decreases the rate of injection of chlorine from the pilot chlorinator 30 by adjusting the feedback pilot control signal 64 accordingly. For instance, if the level of chlorine residual is too low, the pilot chlorinator 30 has its flow rate increased. If the level of chlorine residual is too high, the pilot chlorinator 30 has its flow rate decreased.

A magnitude of increase or decrease of the feedback pilot control signal 64 can be calculated to match a degree to which the level of residual free chlorine differs from the set point. Such a magnitude specific version of the system 10 would tend to more quickly adjust chlorine injection rates to return the system 10 to optimal performance. Preferably, rather than blocking the feed forward process control signal 66 when the analyzer 50 measures unacceptable levels of residual free chlorine, the feed forward process control signal 66 can merely be adjusted along with the feedback pilot control signal 64, with appropriate amplification by the ratio of flow rates measured by the flow meters 14, 24, so that the chlorinator 70 most quickly receives adjustments to the feed forward process control signal 66. In this way adjustments are not delayed which return the level of injection of chlorine from the main chlorinator 70 back to an optimal rate of injection.

Preferably, the feed forward process control signal 66 is appropriately timed so that when the chlorinator 70 receives the feed forward process control signal 66, the waste water passing the main chlorine injector 72 is the waste water which was adjacent the waste water which passed into the pilot subsystem 20 and was analyzed by the sample analyzer 50. In this way, if the characteristics of the waste water are fluctuating, the chlorinator 70 adjusts a rate of chlorine delivery into the main conduit 2 at precisely the time necessary to match the change in waste water characteristics inferentially detected by the sample analyzer 50 and communicated to the controller 60. Appropriate delay of the feed forward process control signal 66 includes monitoring the flow rates of the waste water passing through the main stream conduit 2 and through the treatment pathway 26 and also knowing the distances separating the inlet port 22 of the pilot subsystem 20 from the main chlorine injector 72 and the distance from the inlet port 22 of the pilot subsystem 20 to the sample analyzer 50.

With particular reference to FIG. 1, details of the chlorinator 70 are described. The chlorinator 70 would typically take on a general form similar to that of the pilot chlorinator 30 except that the equipment would typically be appropriately sized up to match the delivery needs associated with the size of the main stream conduit 2. Hence, the chlorinator 70 would include some form of throttle, such as any of a variety of different pumps or valves, which receive the feed forward process control signal 66 to control the rate at which chlorine is delivered into the main stream conduit 2. The chlorinator 70 can additionally include a flow meter and feedback signal returning to the controller 60 to verify that the throttle of the chlorinator 70 is operating as desired and verifying that the chlorinator 70 is in fact delivering chlorine at the flow rate which corresponds with the feed forward process control signal 66.

The verification analyzer 80 can take a form similar to that exhibited by the sample analyzer 50 of the pilot subsystem 20. Optionally, the verification analyzer 80 can be left out entirely. Also, the verification analyzer 80 could be appropriately integrated with the sample analyzer 50 so that a single sample analyzer could be used. The analyzer would variously receive samples either from the pilot subsystem 20 to operate the system 10 of this invention or be switched over to act as the verification analyzer 80 and receive a sample from near the outflow 8 of the main stream conduit 2 to verify that the system 10 is operating properly, before being switched back to operate within the pilot subsystem 20. Data from the verification analyzer 80 can be plotted with other output from the controller 80 to allow an operator to monitor and adjust the system 10 for optimal performance.

This disclosure is provided to reveal a preferred embodiment of the invention and a best mode for practicing the invention. Having thus described the invention in this way, it should be apparent that various different modifications can be made to the preferred embodiment without departing from the scope and spirit of this disclosure. When structures are identified as a means to perform a function, the identification is intended to include all structures which can perform the function specified.

What is claimed is:

1. A method for treating a main fluid stream with at least one treatment fluid to precisely alter a selected characteristic of the main fluid stream, the method comprising in combination:

identifying a main fluid stream to be treated and a treatment fluid to be used in altering the main fluid stream;

diverting a pilot stream out of the main fluid stream;

treating the pilot stream by addition of the treatment fluid into the pilot stream at a first location on the pilot stream;

analyzing at least a portion of the pilot stream at a location downstream from the first location, resulting in the measurement of the selected characteristic present in the pilot stream after alteration with the treatment fluid; and using the results of said analyzing step to choose a final amount of treatment fluid to introduce into the main fluid stream.

2. The method of claim 1 wherein said treating step includes the step of adjusting an amount of the treatment fluid to be introduced into the pilot stream at the first location based on the result of said analyzing step.

3. The method of claim 2 including the further step of choosing a set point corresponding with a desired level for the selected characteristic and continuing said adjusting step until said analyzing step results in the selected characteristic having a level matching the set point.

4. the method of claim 3 wherein said using step includes the steps of:

determining a ratio of the main fluid stream flow rate to the pilot stream flow rate, identifying a proper amount of the treatment fluid used in said choosing step to cause the level of the selected characteristic in the pilot stream at the downstream location to match the set point;

multiplying the ratio by the proper amount to establish the final amount of treatment fluid to introduce into the main stream; and introducing the final amount of treatment fluid into the main fluid stream at an injection point.

5. The method of claim 4 including the further step of spacing the first location of said treating step and the downstream location of said analyzing step sufficiently apart to allow a reaction between the treatment fluid and the pilot stream to be substantially completed.

6. The method of claim 5 wherein said identifying step includes establishing the main fluid stream as a waste water stream with bacteria present and establishing the treatment fluid as a chlorine containing compound capable of neutralizing the bacteria in the waste water.

7. The method of claim 6 wherein said choosing step includes the step of setting the set point to represent an acceptable amount of residual chlorine remaining in the waste water.

8. The method of claim 7 wherein said diverting step occurs continuously and said introducing step occurs continuously, such that an amount of the treatment fluid delivered in said introducing step is continuously adjusted to match the needs indicated by the result of said analyzing step.

9. The method of claim 8 including the further step of spacing the treatment fluid main fluid stream injection point downstream from a pilot stream inlet a distance at least as great as a nearest distance equal to a flow rate of the main stream multiplied by an amount of time to complete said analyzing step, such that the main stream has a level of the selected characteristic matching that of the pilot stream when said analysis step occurs.

10. The method of claim 9 including the further step of delaying said introducing step by an amount of time approximately equal to any excess distance the treatment fluid main fluid stream injection point is located beyond the nearest distance, divided by the main stream flow rate.

11. A system for controlling an amount of a selected characteristic in a main fluid stream by introducing a precise amount of a treatment fluid, the system comprising in combination:

a pilot treatment pathway having an inlet port located in the main fluid stream, such that a portion of the main fluid stream is diverted as a pilot fluid stream;

a pilot treatment fluid inlet for addition of treatment fluid into said pilot fluid stream located at a first location on said pilot treatment pathway, said treatment fluid inlet coupled to a source of treatment fluid;

a selected characteristic analyzer located at a second location on said pilot treatment pathway, said second location located downstream from said first location;

a main treatment fluid inlet located on the main fluid stream at a location downstream from said inlet port, said main treatment fluid inlet coupled to a source of treatment fluid; and a throttle located between said main treatment fluid inlet and said source of treatment fluid, said throttle at least partially controlled by said analyzer.

12. The system of claim 11 wherein said system includes a flow meter measuring an amount of the treatment fluid which passes through said pilot treatment fluid inlet, wherein a controller receives said pilot treatment fluid flow meter information and information relating to an amount of the selected characteristic measured by said analyzer and determines a setting for said throttle based on said flow meter information and said analyzer information.

13. The system of claim 12 wherein said controller has a feed forward process control signal outputted therefrom to adjust said throttle.

14. The system of claim 13 wherein a pilot treatment fluid flow rate control signal is sent from said controller to said pilot treatment fluid inlet to adjust an amount of the treatment fluid introduced into said pilot treatment pathway at said pilot treatment fluid inlet.

15. The system of claim 14 wherein a main fluid stream flow rate meter and a pilot fluid stream flow rate meter each measure flow rates for the main fluid stream and the pilot fluid stream, respectively, and provides such main fluid stream and pilot fluid stream flow rate information to said controller.

16. The system of claim 15 wherein the treatment fluid is a chlorine containing substance and wherein the selected characteristic is chlorine residual, and wherein said analyzer is a chlorine residual analyzer.

17. The system of claim 16 wherein a sulphur dioxide injection subsystem interfaces with said pilot treatment pathway such that sulphur dioxide can be introduced into said pilot treatment pathway, said SO2 injection subsystem receiving a control signal from said controller and feeding back sulphur dioxide flow rate information back to said controller.

18. A fluid stream treatment controller for precisely controlling introduction of treatment fluid into a main fluid stream, the controller comprising in combination:

a pilot treatment pathway having an inlet port located in the main fluid stream, such that a portion of the main fluid stream is diverted as a pilot fluid stream;

a pilot treatment fluid inlet located at a first location on said pilot treatment pathway in said diverted pilot fluid stream, said pilot treatment fluid inlet coupled to a source of treatment fluid and having an amount of the treatment fluid passing through said inlet controlled by a pilot treatment fluid flow rate control signal;

a selected characteristic analyzer located at a second location on said pilot treatment pathway downstream from said first location, said selected characteristic analyzer generating a selected characteristic feedback signal corresponding with an amount of the selected characteristic measured by said analyzer;

said treatment fluid flow rate control signal at least partially related to said feedback signal; and a feed forward signal coupled to a main treatment fluid inlet located on the main fluid stream downstream from said inlet port, said main treatment fluid inlet having a throttle located adjacent thereto, said throttle controlled at least partially by said feed forward signal, said feed forward signal at least partially related to said feedback signal from said analyzer.

19. The fluid stream treatment controller of claim 18 wherein said analyzer feedback signal is received by a comparator which compares said analyzer signal with a signal which would correspond to a desired level of the selected characteristic being detected by said analyzer, the difference between said analyzer feedback signal and said desired level corresponding with a magnitude of said pilot treatment fluid control signal and corresponding with a magnitude of said feed forward signal.

20. The controller of claim 19 wherein the ratio of magnitudes of said feed forward signal to said pilot treatment fluid control signal is substantially the same as a ratio of the main fluid stream flow rate to the pilot fluid stream flow rate.

* * * * *